(12) United States Patent
Soler Ranzani et al.

(10) Patent No.: US 8,846,744 B2
(45) Date of Patent: Sep. 30, 2014

(54) PHARMACEUTICAL COMPOSITIONS OF CO-CRYSTALS OF TRAMADOL AND COXIBS

(75) Inventors: Luis Soler Ranzani, Barcelona (ES); Albert Falivene Aldea, Barcelona (ES)

(73) Assignee: Laboratorios del Dr. Esteve, S.A., Barcelona (ES)

(*) Notice: Subject to any disclaimer, the term of this patent is extended or adjusted under 35 U.S.C. 154(b) by 0 days.

(21) Appl. No.: 13/701,192

(22) PCT Filed: Jun. 3, 2011

(86) PCT No.: PCT/EP2011/002749
§ 371 (c)(1),
(2), (4) Date: Dec. 19, 2012

(87) PCT Pub. No.: WO2011/151080
PCT Pub. Date: Dec. 8, 2011

(65) Prior Publication Data
US 2013/0109659 A1 May 2, 2013

(30) Foreign Application Priority Data
Jun. 4, 2010 (EP) .................................. 10384002

(51) Int. Cl.
*A61K 31/415* (2006.01)
*A61K 31/18* (2006.01)
*A61K 31/135* (2006.01)
*A61K 47/34* (2006.01)
*A61K 9/20* (2006.01)
*A61K 47/32* (2006.01)
*A61K 31/4162* (2006.01)
*A61K 31/05* (2006.01)
*A61K 31/63* (2006.01)
*A61K 31/045* (2006.01)

(52) U.S. Cl.
CPC .............. *A61K 47/34* (2013.01); *A61K 31/135* (2013.01); *A61K 31/4162* (2013.01); *A61K 9/2027* (2013.01); *A61K 31/05* (2013.01); *A61K 31/63* (2013.01); *A61K 31/045* (2013.01); *A61K 47/32* (2013.01); *A61K 31/415* (2013.01); *A61K 9/2018* (2013.01); *A61K 31/18* (2013.01)
USPC .......................................... 514/403; 514/602

(58) Field of Classification Search
CPC ..... A61K 31/05; A61K 31/045; A61K 31/63; A61K 31/18; A61K 31/415; A61K 31/4162
USPC .................................................. 514/403, 602
See application file for complete search history.

(56) References Cited

FOREIGN PATENT DOCUMENTS

| DE | 102006044694 A1 | 3/2008 |
| EP | 1138320 A2 | 10/2001 |
| WO | 0051685 A1 | 9/2000 |
| WO | 2008085674 A1 | 7/2008 |
| WO | 2010043412 A1 | 4/2010 |

OTHER PUBLICATIONS

Kim et al, "Solubility Enhancers for Oral Drug Delivery", American Journal of Drug Delivery, vol. 2, No. 2, pp. 113-130 (Jun. 2004) (abstract).*
International Search Report for PCT/EP2011/002749 dated Jul. 7, 2011.
Shan N et al; "The role of cocrystals in pharmaceutical science," Drug Discovery Today, May 1, 2008, pp. 440-446, vol. 13, No. 9-10.

* cited by examiner

*Primary Examiner* — Kevin E Weddington
(74) *Attorney, Agent, or Firm* — Heslin Rothenberg Farley & Mesiti P.C.

(57) ABSTRACT

The present invention relates to oral pharmaceutical compositions comprising co-crystals of tramadol and celecoxib and processes for the preparation of these oral pharmaceutical compositions. The present invention also relates to methods of using oral pharmaceutical compositions comprising co-crystals of tramadol and celecoxib as medicaments, more particularly for the treatment of pain.

25 Claims, 6 Drawing Sheets

PHARMACEUTICAL COMPOSITIONS OF CO-CRYSTALS OF TRAMADOL AND COXIBS

CROSS REFERENCE TO RELATED APPLICATIONS

This application is a U.S. National Phase filing under 35 U.S.C. §371 of International Application PCT/EP2011/002749, filed Jun. 3, 2011, and published as WO 2011/151080 on Dec. 8, 2011. PCT/EP2011/002749 claimed benefit of priority from European Application 10384002.1, filed Jun. 4, 2010. The entire contents of each of the prior applications are hereby incorporated herein by reference.

The present invention relates to oral pharmaceutical compositions comprising co-crystals of tramadol and celecoxib, processes for preparation of the same and their use as medicaments, more particularly for the treatment of pain.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus.

In general, pain conditions can be divided into chronic and acute. Chronic pain includes neuropathic pain and chronic inflammatory pain, for example arthritis, or pain of unknown origin, as fibromyalgia. Acute pain usually follows non-neural tissue injury, for example tissue damage from surgery or inflammation, or migraine.

Many drugs are known to be useful in the treatment or management of pain including opioids, while derivatives of morphine are indicated for the treatment of moderate to severe, chronic and acute pain in human. The analgesic effect is obtained through their action on morphinic receptors, preferably the p-receptors. One of the morphinic derivatives that has shown very good results when orally administrated is tramadol. Tramadol, whose chemical name is 2-(dimethylaminomethyl)-1-(3-methoxyphenyl)cyclohexanol, has the following formula:

Tramadol

This structure shows two different chiral centers and thus may exist in different diastereoisomers among which the tramadol is the cis-diastereisomer: (1R,2R), or (1S,2S), both also known as (+)-tramadol and (−)-tramadol and both of which contribute in different ways to its activity. Even though a well-used drug tramadol still shows a number of side effects (most of them dose related) like constipation; diarrhea; dizziness; drowsiness; dry mouth; headache; nausea; trouble sleeping; vomiting; weakness. Reducing the necessary dosage of tramadol (e.g. by a new drugable form and/or formulation including tramadol) for the treatment of pain to achieve an analgesic effect would thus be quite advantageous A further well-known analgesic compound is celecoxib. Celecoxib is an anti-inflammatory and pain killer drug and it is one of the most frequently used agents in the treatments of chronic musculo-skeletal inflammatory illnesses. Celecoxib, 4-[5-(4-methylphenyl)-3-(trifluoromethyl)pyrazol-1-yl]benzenesulfonamide has the following formula:

Celecoxib is an oral, highly selective cyclooxygenase-2 (COX-2) inhibitor, and it is indicated for the treatment of symptomatic relief in the treatment of osteoarthritis, rheumatoid arthritis and ankylosing spondylitis (Goldenberg MM. (1999). Celecoxib, a selective cyclooxygenase-2 inhibitor for the treatment of rheumatoid arthritis and osteoarthritis. *Clin Ther.* 21, 1497-513). This high selectivity allows celecoxib and other COX-2 inhibitors to reduce inflammation (and pain) while minimizing gastrointestinal adverse drug reactions (e.g. stomach ulcers) that are common with non-selective NSAIDs.

The enzyme cyclooxygenase is responsible for generation of prostaglandins. Two isoforms, COX-1 and COX-2, have been identified. COX-2 is the isoform of the enzyme that has been shown to be induced by pro-inflammatory stimuli and has been postulated to be primarily responsible for the synthesis of prostanoid mediators of pain, inflammation, and fever. COX-2 is also involved in ovulation, implantation and closure of the ductus arteriosus, regulation of renal function, and central nervous system functions (fever induction, pain perception and cognitive function). It may also play a role in ulcer healing. COX-2 has been identified in tissue around gastric ulcers in man but its relevance to ulcer healing has not been established.

Celecoxib is well-known to be practically insoluble in water, putting clear limitations on its use in pharmaceutical formulations.

Celecoxib is a very weak acid molecule (pKa11.1) (http://www.medsafe.govt.nz/profs/Datasheet/c/Celebrexcap.htm) that is non ionized form in all physiological ranges of pH. It is a high permeable drug, but with very low water solubility (7 ug/ml) (Neelam Seedher, Somm Bhatia, 2003 "Solubility enhancement of Cox-2 Inhibitors Using various Solvent Systems", AAPS Pharm. Sci. Tech, 4(3), 1-9). These physicochemical properties make celecoxib to be considered class II in the Biopharmaceutical Classification System (BCS) (Mehran Yazdanian, Katherine Briggs, Corinne Jankovskty, Amale Hawi, 2004, "The "High solubility" Definition of the Current FDA Guidance on Biopharmaceutical Classification System May Be Too Strict for Acidic Drugs", Pharm Res, 21(2), 295). Consequently the extent of celecoxib oral absorption appears to be limited by its bad solubility and slow dissolution rate, which leads to and inadequate dissolution in gastrointestinal fluids (Susan K. Paulson, Margaret B.

Vaughn, Susan M. Jessen, Yvette Lawal, Christopher J. Gresk, Bo Yan, Timothy J. Maziasz, Chyung S. Cook. Aziz Karim, 2001, "Pharmacokinetics of Celecoxib after Oral Administration in Dogs and Humans: Effect of Food Site of Absorption", J. Pharmacol. & Experim Therapeutics, 297(2), 638-645).

The marketed formulation Celebrex®, that is administered orally, contains celecoxib (free acid) crystalline form and has an absolute bioavailability ranging from 20-40% in dogs attributed to a reduced absorption (Susan K. Paulson et al., 2001; see above). This poor bioavailability limits distribution and target organ delivery, hence efficacy of this drug.

Recently a new co-crystal of tramadol and celecoxib has been described as example 4 in the PCT-publication WO 2010/043412 being the co-crystal of (rac)-tramadol.HCl-celecoxib (1:1) characterized in detail in this example 4. This co-crystal forms a very stable and drugable new chemical entity that provide new means of improving the properties of tramadol, especially in regard to the treatment of pain. The co-crystal shows—in pain indications—a clear synergism if compared to celecoxib and tramadol. In addition, the co-crystal seems to possibly display (in-vivo) an improved bioavailability regarding celecoxib exposure compared to administration of celecoxib alone and to the physical mixture of celecoxib and tramadol.

Still, in the art there is not yet any concrete pharmaceutical formulation described that would allow these new co-crystal to display these advantages or even improve them, when used in a true medical application e.g when using it for human medication. Accordingly, there is a need to have a formulation for this new co-crystal published as Example 4 of WO 2010/043412 that preserves the properties of the co-crystal or can even improve them.

It was therefore the overall aim of this invention to provide an oral formulation comprising the co-crystal of (rac)-tramadol.HCl and celecoxib (1:1) as described in WO 2010/043412, example 4.

The desired oral formulation aimed-at by this invention should still maintain the co-crystal structure of (rac)-tramadol.HCl and celecoxib (1:1) This property has or may have the advantage that improved properties resting in the crystalline co-crystal structure are maintained and that in general keeping crystalline structures in an oral formulation is often quite advantageous.

Further properties of the desired oral formulation aimed-at by this invention that would also be highly advantageous are enhanced stability and/or solubility of the comprised active agents of the co-crystal.

Especially desirable improvements/advantages of the formulation of the co-crystal of (rac)-tramadol.HCl-celecoxib (1:1) would include:
- maintain the properties and the physical characteristics of the co-crystal once formulated
- improvement of physicochemical properties of the co-crystal to enhance the absorption and/or the bioavailability
- being easily obtainable, easy to manufacture
- allowing better dissolution rates, especially if dissolving in an aqueous physiological surrounding
- modulate oral absorption for both active principles
- maintain or improve bioavailability of tramadol and improve solubility of celecoxib as such or of any pharmaceutical composition comprising celecoxib
- same exposure for tramadol and/or improve absorption of celecoxib as such or of any pharmaceutical composition comprising tramadol or celecoxib, respectively
- being not dependent of particle size of co-crystal; or
- to be and/or remain essentially free of agglomerates; or if given to a patient
- to decrease the inter- and intra-subject variability in blood levels; or
- to show a good absorption rate (e.g. increases in plasma levels or AUC); or
- to show a high maximum plasma concentration (e.g. $C_{max}$); or
- to show decreased time to peak drug concentrations in plasma ($t_{max}$); or
- to show changes in half life of the compound ($t_{1/2}$), in whichever direction this change is preferably directed.

Other desirable improvements/advantages of the new oral composition would include being (more) active in diseases or symptoms being or related to pain and its subtypes, especially those in which current treatment is insufficient like sciatica or frozen shoulder or pain related to central sensitization (central pain syndrome).

Most desirably the new drugable forms should combine more than one, most of these advantages.

This objective was achieved by providing a (oral) pharmaceutical composition comprising a co-crystal of (rac)-tramadol.HCl-celecoxib (1:1) and at least a solubility enhancer polymer. Preferably this pharmaceutical composition would comprise 10 to 50 weight-% of the co-crystal of (rac)-tramadol.HCl-celecoxib (1:1), preferably 15 to 40 weight-%, most preferably 20 to 30 weight-%.

As shown in more detail in the experimental part, as one example the (oral) pharmaceutical composition according to the invention showed the same exposure of tramadol and was at the same time able to modulate tramadol peak concentrations to lower values if compared to the marketed tramadol product (Adolonta®) thus ensuring efficacy while reducing secondary effects. In respect to celecoxib the (oral) pharmaceutical composition according to the invention showed at the same time an increased absorption resulting in a better bioavailability.

"Solubility enhancer polymer" is defined as polymers able to improve in an oral delivery system the poor solubility of the active agent (e.g. celecoxib). Examples include polyvinyl caprolactam-polyvinyl acetate-polyethylene glycol graft copolymer, copovidone or cyclodextrin. A solubility enhancer polymer could be understood as those polymers whose inclusion in the formulation results in a release that—compared to the formulation without any of them—has a dissolution ratio>1 (see example 1 and FIGS. 1 and 2.). In a general approach "Solubility enhancer polymer" is a polymer defined by its function, the increase of solubility especially of orally applicable drugs. This is an expression well-used and understood in the art (see e.g. Title (and related Abstract) of Kim and Park, American Journal of Drug Delivery, Vol. 2, No. 2, (2004) pp. 113-130(18).

"(1:1)" is defined here as meaning that in the co-crystal the molecular ratio of (rac)-tramadol.HCl and celecoxib is 1:1.

The pharmaceutical composition according to the invention advantageously maintains the co-crystal structure in the formulation and if dissolved enhances the drug release rate of celecoxib and/or tramadol if compared to the co-crystal alone. There seems to be an increase in bioavailability if compared to celecoxib and tramadol raw pure drugs and reference products. Also the formulation of the co-crystal of (rac)-tramadol.HCl-celecoxib (1:1) has an enhanced stability.

In a preferred embodiment the percentage of co-crystal of (rac)-tramadol.HCl-celecoxib (1:1) dissolved from the pharmaceutical composition according to the invention in a physiological fluid or a fluid simulating a physiological fluid (like 0.1 N HCl solution with 2% SLS (Sodium Lauryl Sulphate) or buffer solution of pH 12 with 1% SLS)—especially in alkaline fluids—within the first 30 minutes would be more than 85% and/or within the first 45 minutes would be more than 90% (e.g. in a USP paddle test).

In a preferred embodiment the "Solubility Enhancer Polymers" were selected from caprolactam-polyvinyl acetate-polyethylene glycol graft copolymer (Soluplus®) or other hydrophilic polymers like copovidone (a copolymer of 1-vinyl-2-pyrrolidone and vinyl acetate; Kollidon® VA 64), povidone, poloxamers (nonionic polyoxyethylene-polyoxypropylene copolymers as p. ex Lutrol®), cyclodextrin (Kleptose®), polyethylene glycol and derivatives (PEGs) and glyceryl behenate (Gelucire®) or were selected from polyvinyl caprolactam-polyvinyl acetate-polyethylene glycol graft copolymer (Soluplus®) or other hydrophilic polymers like copovidone (a copolymer of 1-vinyl-2-pyrrolidone and vinyl acetate; Kollidon® VA 64), povidone, poloxamers (nonionic polyoxyethylene-polyoxypropylene copolymers as p. ex Lutrol®), cyclodextrin (Kleptose®), polyethylene glycol and derivatives (PEGs) and lauroyl macrogol-32 glycerides EP (Gelucire 44/14®). Preferably the "Solubility Enhancer Polymers" were selected from caprolactam-polyvinyl acetate-polyethylene glycol graft copolymer (Soluplus®) or other hydrophilic polymers like or selected from copovidone (a copolymer of 1-vinyl-2-pyrrolidone and vinyl acetate; Kollidon® VA 64), povidone, or poloxamers (nonionic polyoxyethylene-polyoxypropylene copolymers as p. ex Lutrol®; or were selected from polyvinyl caprolactam-polyvinyl acetate-polyethylene glycol graft copolymer (Soluplus®) or other hydrophilic polymers like or selected from copovidone (a copolymer of 1-vinyl-2-pyrrolidone and vinyl acetate; Kollidon® VA 64), povidone, or poloxamers (nonionic polyoxyethylene-polyoxypropylene copolymers as p. ex Lutrol®. The best results were obtained with Soluplus® and copovidone (Kollidon® VA 64).

Accordingly in one preferred embodiment of the pharmaceutical composition according to the invention the solubility enhancer polymer is selected from polyvinyl caprolactam-polyvinyl acetate-polyethylene glycol graft copolymer or other hydrophilic polymers like copovidone, povidone, poloxamers, cyclodextrin, polyethylene glycol and lauroyl macrogol-32 glycerides EP, preferably selected from polyvinyl caprolactam-polyvinyl acetate-polyethylene glycol graft copolymer or other hydrophilic polymers selected from copovidone, povidone, or poloxamers. In another embodiment of the pharmaceutical composition according to the invention the solubility enhancer polymer is selected from caprolactam-polyvinyl acetate-polyethylene glycol graft copolymer or other hydrophilic polymers like copovidone, povidone, poloxamers, cyclodextrin, polyethylene glycol and glyceryl behenate, preferably selected from caprolactam-polyvinyl acetate-polyethylene glycol graft copolymer or other hydrophilic polymers like or selected from copovidone, povidone, or poloxamers.

In a very preferred embodiment of the pharmaceutical composition according to the invention the solubility enhancer polymer is polyvinyl caprolactam-polyvinyl acetate-polyethylene glycol graft copolymer (Soluplus®). In another embodiment of the pharmaceutical composition according to the invention the solubility enhancer polymer is caprolactam-polyvinyl acetate-polyethylene glycol graft copolymer (Soluplus®).

Soluplus® is a polyvinyl caprolactam-polyvinyl acetate-polyethylene glycol graft copolymer (registered trademark of BASF Corporation).

In another very preferred embodiment of the pharmaceutical composition according to the invention the solubility enhancer polymer is copovidone.

Copovidone is a copolymer of 1-vinyl-2-pyrrolidone and vinyl acetate. A commercial example is Kollidon® VA 64 (registered trademark of BASF Corporation). Kollidon® VA 64 (copovidone) is a vinylpyrrolidone-vinyl acetate copolymer that is soluble both in water and in alcohol. The ratio vinylpyrrolidone:vinyl acetate in the copolymer is 6:4. This polymer is highly hydrophilic resulting in a higher wetting of the co-crystal of tramadol and celecoxib and improvement of drug solubility.

The quantity of solubility enhancer polymer used in the pharmaceutical composition according to the invention lies between 2-50 weight-%, preferably between 8-12 weight-%. There seems to be no marked increase in drug release rate of celecoxib when the level of solubility enhancer polymer in the pharmaceutical composition according to the invention is raised beyond 8-12 weight-%. Therefore, considering these results a preferred level of solubility enhancer polymer will be approximately 8 weight-%.

Accordingly in a preferred embodiment of the pharmaceutical composition according to the invention the content of solubility enhancer polymer used in the formulation according to the invention lies between 2-50 weight-%, preferably between 8-12 weight-% or approximately 8 weight-%.

Co-crystal of (rac)-tramadol.HCl-celecoxib (1:1) could be formulated as tablets obtained by direct compression method well-known in the art. This is a most suitable manufacturing technology as it is the less aggressive to the co-crystal structure, it seems to show the best results in solubility enhancement and also it is—at least one of—the most economical manufacturing way/s. Furthermore, co-crystals of (rac)-tramadol.HCl-celecoxib (1:1) could be also formulated as powder capsules, dry granulation, slurries and dry roller compaction.

In another preferred embodiment the pharmaceutical composition according to the invention takes on a form selected from tablet, powder capsules, or is formulated by dry granulation, slurries and dry roller compaction, preferably is in form of a tablet, most preferably is in form of a tablet producible obtainable by a direct compression process.

Accordingly, another preferred embodiment of the pharmaceutical composition according to the invention takes the form of a tablet comprising a co-crystal of (rac)-tramadol.HCl-celecoxib (1:1) and at least a solubility enhancer polymer obtainable by a direct compression process.

A parallel aspect of the invention refers to an (oral) pharmaceutical composition in form of a tablet comprising a co-crystal of (rac)-tramadol.HCl-celecoxib (1:1) obtainable by a direct compression process, which preferably comprises at least a solubility enhancer polymer (as defined above) or is blended before a direct compression process, which most preferably is blended with at least a solubility enhancer polymer before the direct compression process. Preferably this pharmaceutical composition would comprise 10 to 50 weight-% of the co-crystal of (rac)-tramadol.HCl-celecoxib (1:1), preferably 15 to 40 weight-%, most preferably 20 to 30 weight-%.

The co-crystal of (rac)-tramadol.HCl-celecoxib (1:1) could be blended (e.g. with solubility enhancer polymer) and directly compressed with at least a solubility enhancer polymer in order to enhance drug solubility of celecoxib. Tablets with direct compression process or blending/direct compression methods, improve drug release of celecoxib. Therefore, the direct compression process is recommended due to economic considerations and to prevent possible structural changes of the co-crystal.

In some preferred embodiments concerning the direct compression process, the compression force applied during the direct compression process could be 0.5 kN to 75 kN.

Surfactants (=surfactant polymers) may help to enhance drug solubility. Surfactants can be selected from anionic, cationic or neutral. The surfactants/polymers selected were: sodium lauryl sulfate (SLS), Sepitrap 80® (Microencapsulated polisorbate 80) and Sepitrap 4000® (Microencapsulated polyoxyl 40-hydrogenated castor oil). Preferably the pharmaceutical composition according to the invention would comprise 1 to 20 weight-% of the surfactant/s, preferably 2 to 15 weight-%, most preferably 3 to 10 weight-%.

In another preferred embodiment the pharmaceutical composition according to the invention comprising a co-crystal of (rac)-tramadol.HCl-celecoxib (1:1) further comprises at least a surfactant, with preferably the surfactant polymer being selected from microencapsulated polisorbate 80, microencapsulated polyoxyl 40-hydrogenated castor oil and sodium lauryl sulphate. In such a preferred embodiment, the pharmaceutical composition according to the invention comprising a co-crystal of (rac)-tramadol.HCl-celecoxib (1:1) and at least a solubility enhancer polymer obtainable by a direct compression process further comprises at least a surfactant, with preferably the surfactant polymer being selected from microencapsulated polisorbate 80, microencapsulated polyoxyl 40-hydrogenated castor oil and sodium lauryl sulphate.

The direct compression process requires good rheological characteristics, good compressibility of the blend formulated and also a good uniformity of the blend to ensure a correct dosing and a good productivity at commercial scale. Fillers are usually part of a tablet formulation. The filler selection must take care of the deformation behavior of the filler and the rheological properties, in order to obtain a balanced formulation, free flowing co-processed excipients specifically designed for direct compression process, well known excipients with plastically deformation behavior are considered. Moreover, the water solubility of the excipients must also be considered in order to help the tablet to achieve a good disintegration and a fast dissolution of the API. The soluble fillers selected are within family of sugars as xylitol, sorbitol, isomalt, erythritol, sucrose, fructose, dextrose most preferable spray dried mannitol and lactose family; as insoluble filler calcium phosphate, calcium carbonate, most preferable microcrystalline celluloses were considered for the formulation of the co-crystal: MCC 102 (90 μm) and MCC 200 (200 μm) or compounds as silicified microcrystalline or Prosolv® Easytab (a composite containing microcrystalline cellulose, colloidal silicon dioxide, sodium starch glycolate and sodium stearyl fumarate) or Prosolv SMCC (a composite Silicified Microcrystalline Cellulose).

The fillers selected for the examples are spray-dried mannitol and microcrystalline cellulose which are fillers that show good flow properties.

A lubricant (or lubricant excipient) can be introduced in the formulation in order to optimize the flow properties of the formulation and prevent the adhesion to the punches during the compression process. Lubricants can be selected from stearyl fumarate, magnesium stearate, talc, hydrophilic fumed silica (Aerosil® 200). The lubricants selected for the examples are stearyl fumarate and talc.

A disintegrant can be introduced in the formulation in order to promote the breakup of the tablet into smaller fragments in an aqueous environment thereby promoting a more rapid release of the drug substance. Disintegrants can act through three major mechanisms: swelling, wicking and deformation. Disintegrants can be selected from crospovidone, croscarmelose sodium, sodium starch glycolate, pregelatinized starch, starch, polacrilin potassium, low-substituted hydroxypropyl cellulose (L-HPC), calcium carboxymethylcellulose, alginic acid. The disintegrant selected for the examples is crospovidone.

Accordingly, in a preferred embodiment of the pharmaceutical composition according to the invention the composition comprises at least one further pharmaceutically acceptable excipient like a filler, a disintegrant and/or a lubricant.

In a preferred embodiment of the pharmaceutical composition according to the invention the filler is selected from sugars such as xylitol, sorbitol, isomalt, erythritol, sucrose, fructose, dextrose most preferable spray dried mannitol and lactose family or from insoluble fillers like calcium phosphate, calcium carbonate or microcrystalline celluloses like MCC 102 (90 μm) and MCC 200 (200 μm) or other compounds such as silicified microcrystalline or compositions containing microcrystalline cellulose, colloidal silicon dioxide, sodium starch glycolate and sodium stearyl fumarate, preferably are selected from sugars such as xylitol, sorbitol, isomalt, erythritol, sucrose, fructose, dextrose most preferable spray dried mannitol and lactose family or from microcrystalline cellulose, most preferably are selected from spray dried mannitol and microcrystalline cellulose. Preferably the content of filler/s of the pharmaceutical composition according to the invention is selected between 20 to 80 weight-%, preferably 30 to 70 weight-% or 40 to 60 weight-%.

In a preferred embodiment of the pharmaceutical composition according to the invention the lubricant is selected from stearyl fumarate, magnesium stearate, talc, hydrophilic fumed silica (like Aerosil® 200), preferably are selected from stearyl fumarate and talc. Preferably the pharmaceutical composition according to the invention would comprise 0.5 to 10 weight-% of the lubricant/s, preferably 1 to 5 weight-%.

In a preferred embodiment of the pharmaceutical composition according to the invention the disintegrant is selected from crospovidone, croscarmelose sodium, sodium starch glycolate, pregelatinized starch, starch, polacrilin potassium, low-substituted hydroxypropyl cellulose (L-HPC), calcium carboxymethylcellulose, alginic acid, preferably is crospovidone. Preferably the pharmaceutical composition according to the invention would comprise 1 to 20 weight-% of the disintegrant, preferably 2 to 15 weight-%, most preferably 3 to 10 weight-%.

Most preferably the co-crystal of (rac)-tramadol.HCl and celecoxib (1:1) comprised in the (oral) pharmaceutical compositions according to the invention is the co-crystal of (rac)-tramadol.HCl and celecoxib (1:1) described and characterized (also with examples of production) in Example 4 of WO 2010/043412.

Accordingly, in a highly preferred embodiment of the pharmaceutical composition according to the invention, the co-crystal of (rac)-tramadol.HCl and celecoxib (1:1) comprised in the (oral) pharmaceutical composition shows a Powder X-Ray Diffraction pattern with peaks [2θ] at 7.1, 9.3, 10.2, 10.7, 13.6, 13.9, 14.1, 15.5, 16.1, 16.2, 16.8, 17.5, 18.0, 19.0, 19.5, 19.9, 20.5, 21.2, 21.3, 21.4, 21.8, 22.1, 22.6, 22.7, 23.6, 24.1, 24.4, 25.2, 26.1, 26.6, 26.8, 27.4, 27.9, 28.1, 29.1, 29.9, 30.1, 31.1, 31.3, 31.7, 32.5, 32.8, 34.4, 35.0, 35.8, 36.2 and 37.2[°].

The 2θ values were obtained using copper radiation ($Cu_{K\alpha 1}$ 1.54060 Å).

Further in this highly preferred embodiment of the pharmaceutical composition according to the invention, the co-crystal of (rac)-tramadol.HCl and celecoxib (1:1) comprised in the (oral) pharmaceutical composition shows a Fourier Transform Infra Red pattern with absorption bands at 3481.6 (m), 3133.5 (m), 2923.0 (m), 2667.7 (m), 1596.0 (m), 1472.4 (m), 1458.0 (m), 1335.1 (m), 1288.7 (m), 1271.8 (m), 1168.7 (s), 1237.3 (m), 1168.7 (s), 1122.6 (s), 1100.9 (m), 1042.2 (m), 976.8 (m), 844.6 (m), 820.1 (m), 786.5 (m) 625.9 (m) cm$^{-1}$.

Further in this highly preferred embodiment of the pharmaceutical composition according to the invention, the co-crystal of (rac)-tramadol.HCl and celecoxib (1:1) comprised in the (oral) pharmaceutical composition has an orthorhombic unit cell with the following dimensions:
a=11.0323(7) Å
b=18.1095(12) Å
c=17.3206(12) Å

Further in this highly preferred embodiment of the pharmaceutical composition according to the invention the co-crystal of (rac)-tramadol.HCl and celecoxib (1:1) comprised in the (oral) pharmaceutical composition shows an endothermic sharp peak of the co-crystal corresponding to the melting point having an onset at 164° C.

Another embodiment of the present invention relates to a process for the production of an oral pharmaceutical composition according to the invention as described above comprising the steps of:
(a) blending the co-crystal of (rac)-tramadol.HCl-celecoxib (1:1) (as described for example in example 4 of WO 2010/043412) with at least a solubility enhancer polymer and optionally one or more filler, disintegrant or surfactant polymer or any combination thereof;
(b) optionally adding at least a lubricant;
(c) directly compressing the blend from step (a) or the lubricated blend from step (b) into a tablet.

In a preferred embodiment of the process according to the invention a filler is mixed into the blend of step (a).

The pharmaceutical compositions according to the present invention are useful in treatment of pain, preferably acute pain, chronic pain, neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica.

Accordingly, a further aspect of the invention also refers to a pharmaceutical composition according to the present invention comprising the co-crystal of (rac)-tramadol.HCl and celecoxib (1:1) for the treatment of pain, preferably acute pain, chronic pain, neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. Another aspect of the invention also refers to the use of a pharmaceutical composition according to the present invention comprising the co-crystal of (rac)-tramadol.HCl and celecoxib (1:1) in the production of a medicament for the treatment of pain, preferably acute pain, chronic pain, neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. In a further aspect the invention also refers to a method of treatment of pain, preferably acute pain, chronic pain, neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica by providing to a patient in need thereof a sufficient amount of a co-crystal by applying a pharmaceutical composition according to the invention as described above.

"Pain" is defined by the International Association for the Study of Pain (IASP) as "an unpleasant sensory and emotional experience associated with actual or potential tissue damage, or described in terms of such damage (IASP, Classification of chronic pain, 2$^{nd}$ Edition, IASP Press (2002), 210). Even though pain is always subjective its causes or syndromes can be classified. One classification to denominate subtypes of pain would be to divide the general pain syndrome into the subtypes of acute and chronic pain or—according to the pain intensity—into mild, moderate and severe pain. In other definitions the general pain syndrome is also divided into "nociceptive" (caused by activation of nociceptors), "neuropathic" (caused by damage to or malfunction of the nervous system) and pain related to central sensitization (central pain syndrome).

According to the IASP "allodynia" is defined as "a pain due to a stimulus which does not normally provoke pain" (IASP, Classification of chronic pain, 2$^{nd}$ Edition, IASP Press (2002), 210). Even though the symptoms of allodynia are most likely associated as symptoms of neuropathic pain this is not necessarily the case so that there are symptoms of allodynia not connected to neuropathic pain though rendering allodynia in some areas broader than neuropathic pain.

The IASP further draws the following difference between "allodynia", "hyperalgesia" and "hyperpathia" (IASP, Classification of chronic pain, 2$^{nd}$ Edition, IASP Press (2002), 212):

| Allodynia | Lowered threshold | Stimulus and response mode differ |
| --- | --- | --- |
| Hyperalgesia | Increased response | Stimulus and response rate are the same |
| Hyperpathia | Raised threshold; Increased response | Stimulus and response rate may be the same or different |

According to the IASP "neuropathy" is defined as "a primary lesion or dysfunction in the nervous system" (IASP, Classification of chronic pain, 2$^{nd}$ Edition, IASP Press (2002), 211). Neuropathic pain may have central or peripheral origin.

"Sciatica" or "sciatic neuritis is defined herein as a set of symptoms including pain that derive from irritation of the sciatic nerve or its roots, "Frozen shoulder" or "adhesive capsulitis" is defined herein as a symptom wherein the connective tissue surrounding the shoulder joint or the shoulder capsule itself, is causing chronic pain, becoming inflamed and stiff.

"Ankylosing spondylitis" or "Morbus Bechterew" is a chronic, inflammatory arthritis and autoimmune disease. It mainly affects joints in the spine and the sacroilium in the pelvis, causing eventual fusion of the spine.

"Pain related to central sensitization"/"central pain syndrome" is defined within this application as a neurological condition caused by damage to or dysfunction of the central nervous system (CNS), which includes the brain, brainstem, and spinal cord. This syndrome can inter alia be caused by stroke, multiple sclerosis, tumors, epilepsy, brain or spinal cord trauma, or Parkinson's disease.

"Nociceptive pain" is defined as a type of pain caused by activation of nociceptors. It can be divided into somatic and visceral pain. "Visceral pain" is pain generally originating from the organs, whereas "(deep) somatic pain" originates from ligaments, tendons, bones, blood vessels, fasciae and muscles.

The daily dosage to be applied to humans and animals through use of the pharmaceutical compositions according to the invention may vary depending on factors that have their basis in the respective species or other factors, such as age, sex, weight or degree of illness and so forth. The daily dosage for humans preferably is 20 to 1000 mg, preferably 50 to 250 milligrams of the co-crystal of (rac)-tramadol.HCl and celecoxib (1:1) comprised in the pharmaceutical composition according to the invention to be administered during one or several intakes per day. In a preferred embodiment the dosage form of the pharmaceutical composition according to the invention (e.g. a tablet) comprises 50 to 250 (or 100 to 150) milligrams of the co-crystal of (rac)-tramadol.HCl and celecoxib (1:1).

The use of the pharmaceutical composition according to the invention (described above) or the respective method of treatment is preferably related to pain, including nociceptive pain (which includes somatic and visceral pain). These preferred embodiments of the invention may also be related to neuropathic pain and/or to pain related to central sensitization (the so-called "central pain syndrome").

The use of the pharmaceutical composition according to the invention (described above) or the respective method of treatment may preferably also be related to acute and chronic pain.

The uses of the pharmaceutical composition according to the invention (described above) or the respective method of treatment may preferably also be related to mild, to moderate and to severe pain.

The present invention is illustrated below with the help of the following figures and examples. These illustrations are given solely by way of example and do not limit the invention.

EXAMPLES

Example 1

Solubility Enhancer Polymer Screening Study

The aim of this study was to evaluate the effect of the inclusion of different polymeric ingredients in the (rac)-tramadol.HCl-celecoxib (1:1) co-crystal formulation dissolution profile test. Different tablet formulations were prepared including the (rac)-tramadol.HCl-celecoxib (1:1) co-crystal, a compression base (containing microencapsulated polisorbate 80, microencapsulated polyoxyl 40-hydrogenated castor oil, sodium lauryl sulphate, crospovidone, spray dried mannitol, microcrystalline cellulose and sodium stearyl fumarate) and the different polymeric ingredients tested.

The polymeric ingredients tested were: poloxamers (non-ionic polyoxyethylene-polyoxypropylene copolymers: Lutrol®), povidone (Plasdone K30), copovidone (a copolymer of 1-vinyl-2-pyrrolidone and vinyl acetate; Kollidon® VA 64), polyvinyl caprolactam-polyvinyl acetate-polyethylene glycol graft copolymer (Soluplus®) and cyclodextrin (Kleptose®).

The different formulations were prepared following process described in examples 2. After the compression the dissolution profile test of the different tablets obtained was performed.

The in-vitro dissolution profile test were performed with USP apparatus III (paddles) at 37° C. and 50 rpm with 1000 ml of 0.04M phosphate buffer pH 12 in each vessel during 45 min.

Figure 1:
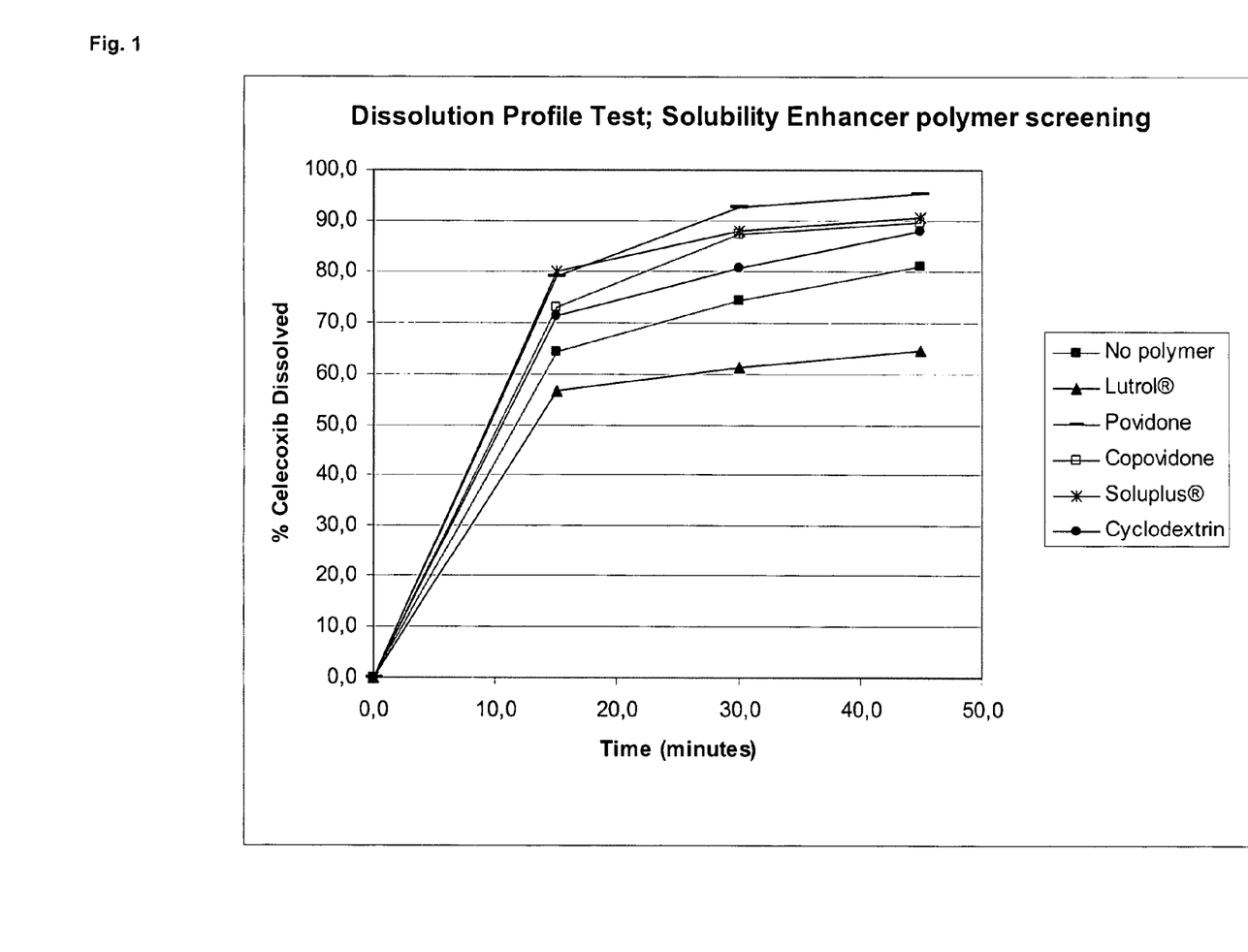
FIG. 1:
Solubility Enhancer polymer screening study. Comparative in-vitro dissolutions profiles

The results of the dissolution profile test are shown in FIG. 1. The faster dissolution profiles were obtained when povidone, copovidone or Soluplus® were included in the tablet formulation. The inclusion of Lutrol® caused a slower dissolution test compared to the tablets that not contain any polymer.

Figure 2:
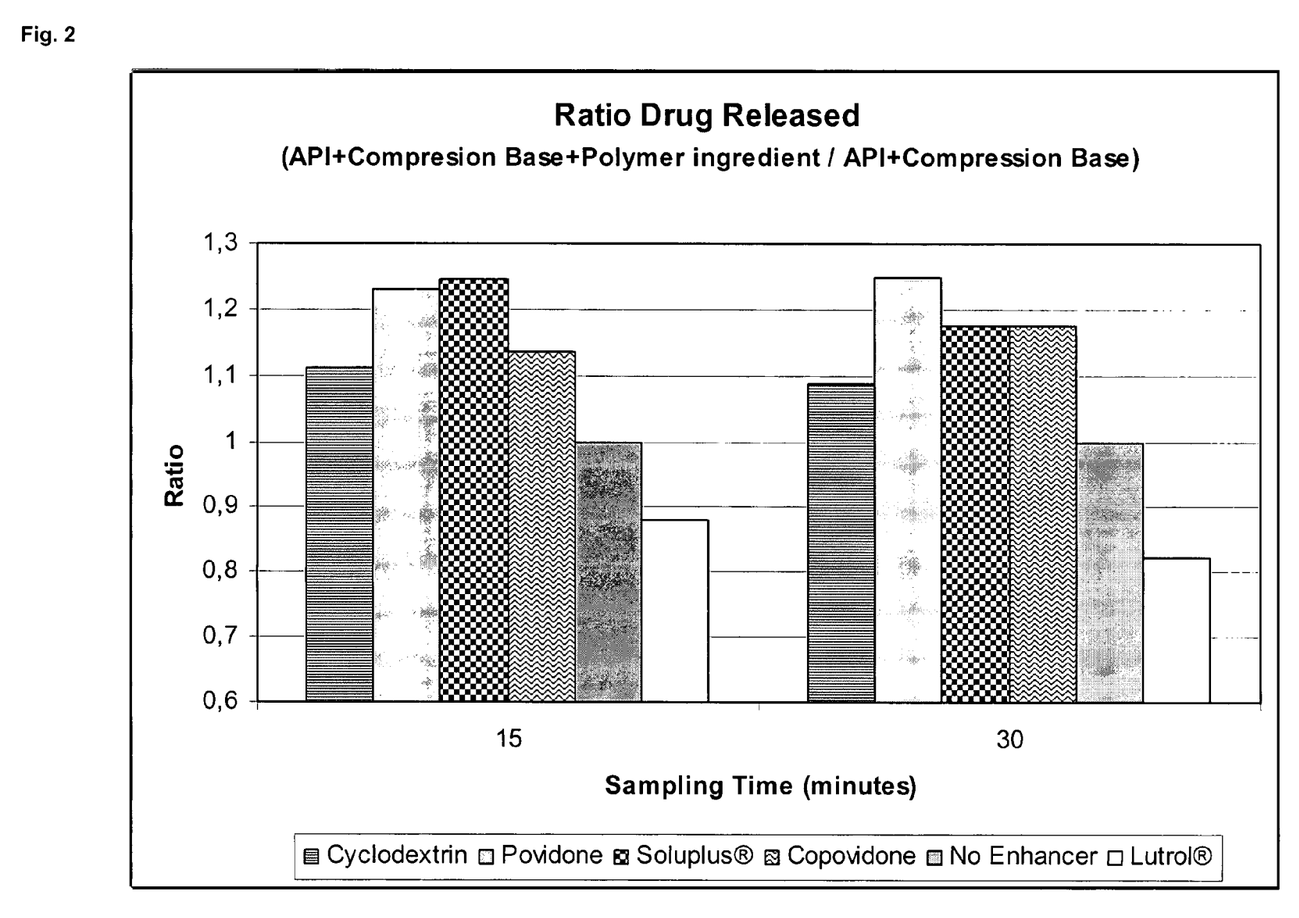
FIG. 2:
Solubility Enhancer polymer screening study. Ratio drug released

The ratio between the amount dissolved of celecoxib at 15 and 30 minutes, with and without polymeric ingredient of the different formulations is calculated from the results obtained in the dissolution profile test. The different ratios are shown in FIG. 2. Based on these results, a solubility enhancer polymer could be understood as those polymers whose inclusion in the formulation results in a release that—compared to the formulation without any of them—has a dissolution ratio>1.

Example 2

Pharmaceutical Formulations/Tablets Prepared According to the Invention

The tablets of the invention were prepared following the process described below.

Co-crystal of (rac)-tramadol-celecoxib (1:1) according to Example 4 of WO2010/043412 is blended in a first step with microencapsulated polisorbate 80, microencapsulated polyoxyl 40-hydrogenated castor oil, sodium lauryl sulphate, crospovidone, spray dried mannitol, microcrystalline cellulose and copovidone (1-vinyl-2-pyrrolidone/vinyl acetate copolymer) or Soluplus.

After this first blending step, the blend is lubricated adding sodium stearyl fumarate and talc.

The lubricated blend is compressed into tablets in rotary tablet press containing 113.5 mg of co-crystal of (rac)-tramadol.HCl-celecoxib (1:1) (480 mg per tablet).

Example 2A

Tablets of Co-Crystal of (rac)-tramadol.HCl-celecoxib (1:1) Prepared by Direct Compression Using Copovidone as a Solubility Enhancer Polymer

| Ingredients | % | mg for Dose (113.5 mg) |
|---|---|---|
| Co-crystal of (rac)-tramadol·HCl-celecoxib (1:1) | 23.65 | 113.50 |
| Sepitrap 80 ® (Microencapsulated polisorbate 80) | 2.08 | 10.00 |
| Sepitrap 4000 ® (Microencapsulated polyoxyl 40-hydrogenated castor oil) | 2.08 | 10.00 |
| Sodium lauryl sulphate | 2.08 | 10.00 |
| Crospovidone | 8.13 | 39.00 |
| Pearlitol ® (Spray dried mannitol) | 25.99 | 124.75 |
| Sodium stearyl fumarate | 1.50 | 7.20 |
| Talc | 0.50 | 2.40 |
| Microcrystalline cellulose | 25.99 | 124.75 |
| Kollidon ® VA 64 (copovidone) | 8.00 | 38.40 |
| TOTAL | 100.0 | 480.0 mg |

Example 2B

Tablets of Co-Crystal of (rac)-tramadol.HCl-celecoxib (1:1) Prepared by Direct Compression Using Soluplus® as a Solubility Enhancer Polymer

| Ingredients | % | mg for Dose (113.5 mg) |
|---|---|---|
| Co-crystal of (rac)-tramadol·HCl-celecoxib (1:1) | 23.65 | 113.50 |
| Sepitrap 80 ® (Microencapsulated polisorbate 80) | 2.08 | 10.00 |
| Sepitrap 4000 ® (Microencapsulated polyoxyl 40-hydrogenated castor oil) | 2.08 | 10.00 |
| Sodium Lauryl Sulphate | 2.08 | 10.00 |
| Crospovidone | 8.13 | 39.00 |
| Pearlitol ® (Spray dried mannitol) | 25.99 | 124.75 |
| Sodium Stearyl Fumarate | 1.50 | 7.20 |
| Talc | 0.50 | 2.40 |
| Microcrystalline cellulose | 25.99 | 124.75 |
| Soluplus ® (Polyvinyl caprolactam-polyvinyl acetate-polyethylene glycol graft copolymer) | 8.00 | 38.40 |
| TOTAL | 100.0 | 480.0 mg |

Example 2C

Tablets of Co-Crystal of (rac)-tramadol.HCl-celecoxib (1:1) Prepared by Direct Compression Using Soluplus® as a Solubility Enhancer Polymer

| Ingredients | % | mg for Dose (100 mg) |
|---|---|---|
| Co-crystal of (rac)-tramadol·HCl-celecoxib (1:1) | 23.65 | 100.00 |
| Sodium Lauryl Sulphate | 2.08 | 8.79 |
| Crospovidone | 8.13 | 34.38 |
| Pearlitol ® (Spray dried mannitol) | 28.07 | 118.69 |
| Sodium Stearyl Fumarate | 1.50 | 6.34 |
| Talc | 0.50 | 2.11 |
| Microcrystalline cellulose | 28.07 | 118.69 |
| Kollidon ® VA 64 (copovidone) | 8.00 | 33.83 |
| TOTAL | 100.0 | 422.8 mg |

Example 3

Dissolution Tests with Tablets According to Examples 2A, 2B and 2C

Figure 3:
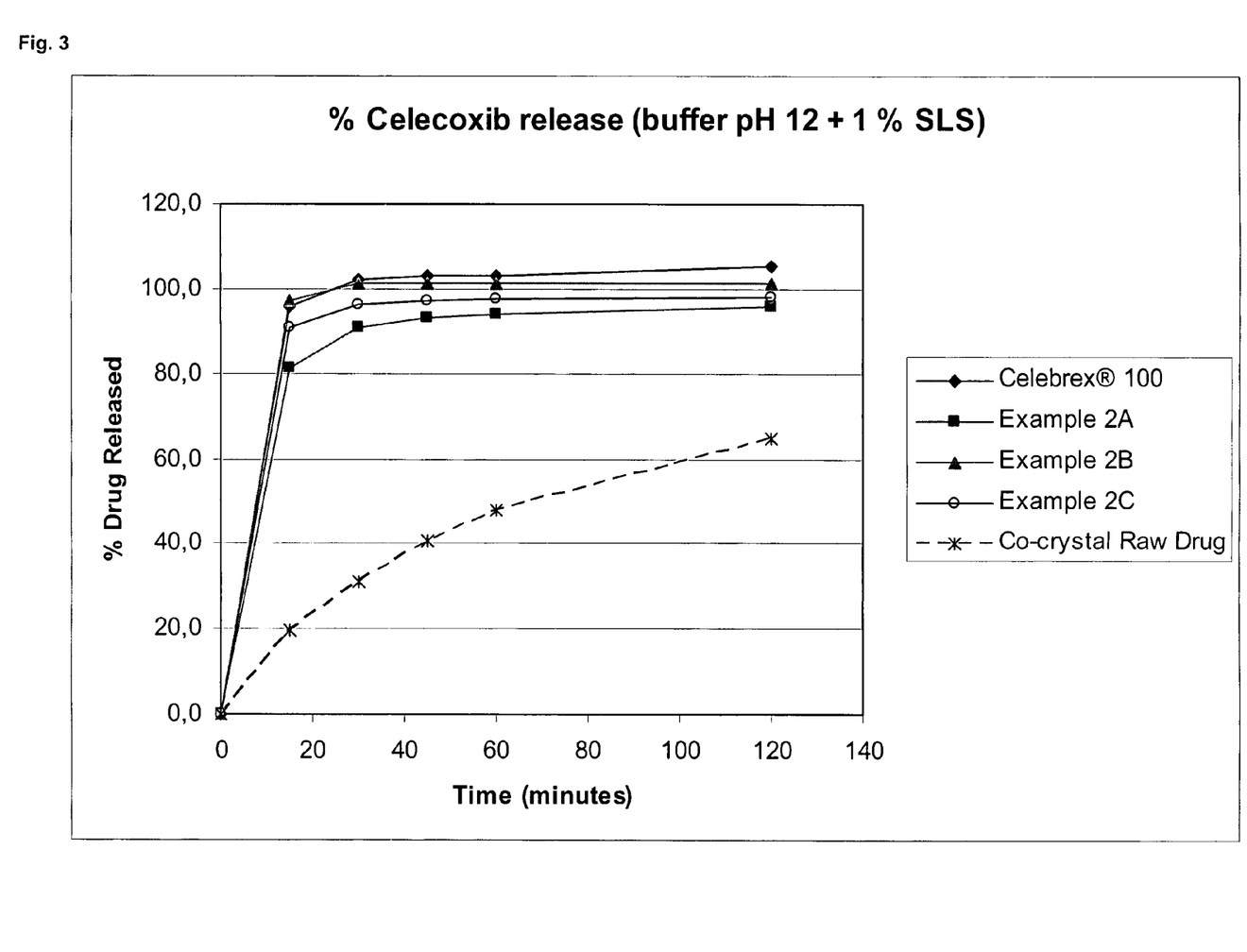
FIG. 3:
Comparative in-vitro dissolution profile (buffer solution pH 12+1% SLS; sodium lauryl sulphate).
Figure 4:
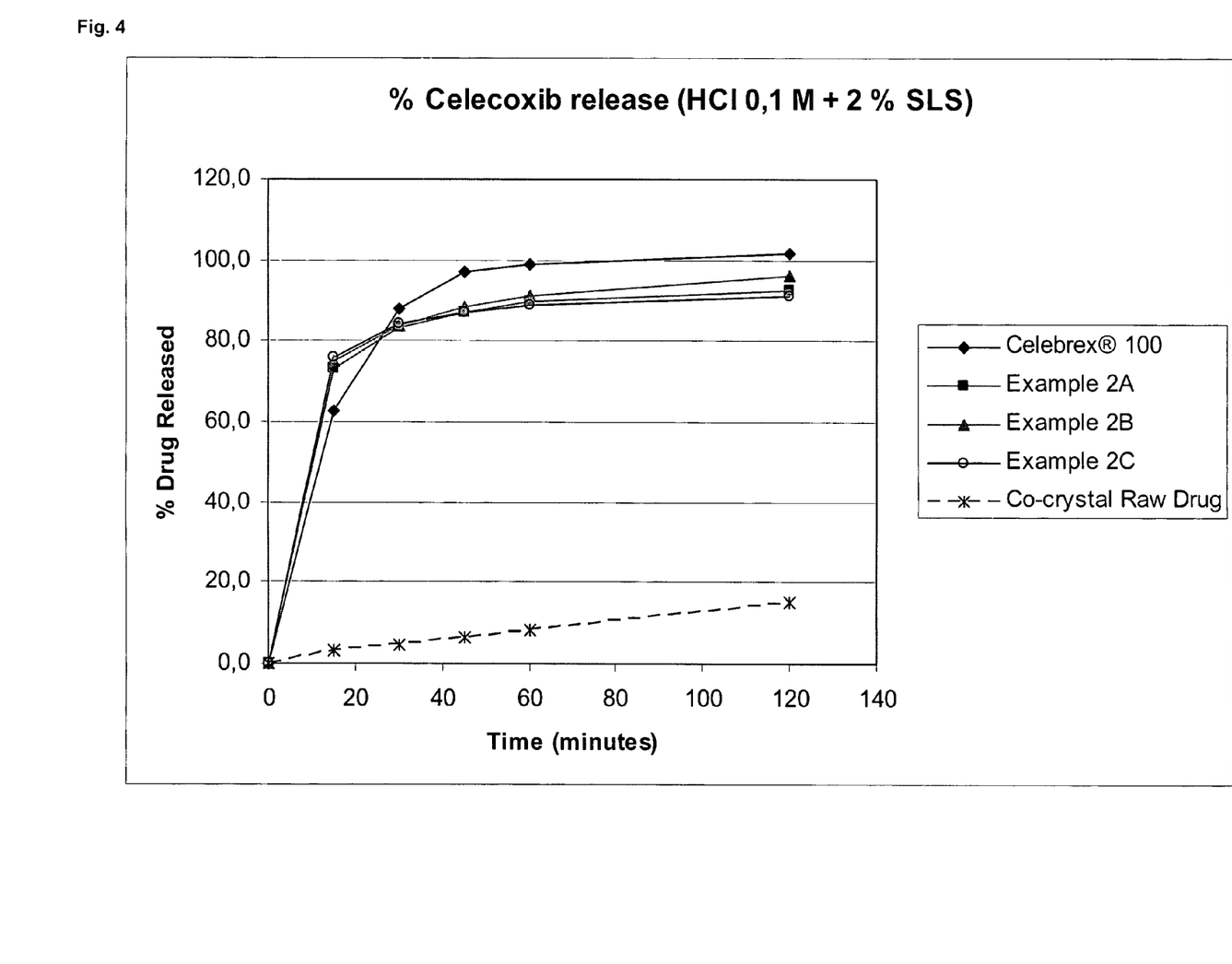
FIG. 4:
Comparative in-vitro dissolution profile (solution HCl 0.1 N+2% SLS; sodium lauryl sulphate)

FIGS. 3 and 4 show the results of in-vitro dissolution tests performed with tablets obtained in examples 2A, 2B and 2C. The release of the co-crystal of (rac)-tramadol.HCl-celecoxib (1:1) from the pharmaceutical compositions of the invention was tested in USP apparatus 2 (paddles) at 37° C. and 50 rpm with 2 hours in buffer solution at pH 12+1% sodium lauryl sulphate (FIG. 3) and in a solution of 0.1 N HCl+2% sodium lauryl sulphate (FIG. 4). Both tests prove that the drug release of celecoxib from the co-crystal of (rac)-tramadol.HCl-celecoxib (1:1) being formulated in the pharmaceutical composition according to the invention is enhanced.

Example 4

Determination of the In Vivo Time Course Profile after Oral Administration of Tablets from Examples 2A, 2B, 2C, in Comparison to Commercial Form of Celecoxib (Celebrex® Capsules) and tramadol.HCl (Adolonta® IR Capsules)

The aim of this study was the comparison of the oral exposure in dogs of tablets from examples 2A, 2B and 2C with the co-administration of marketed oral formulations of celecoxib (Celebrex®) and tramadol.HCl (Adolonta® IR capsules).

In this example the plasma concentration profile vs. time of tramadol and celecoxib was determined after single dose oral administration to fasted dogs, male and females. Similarly pharmacokinetic parameters were calculated by a non-compartmental method.

Tablets from example 2A and 2B were administered in study 1, whereas tablets from example 2C and marketed formulations of celecoxib and tramadol.HCl were evaluated in study 2.

Pharmacokinetic parameters coming from both studies were normalized by the administered dose with the aim of comparing their pharmacokinetic profiles.

Example 4a Study 1

In this study the plasmatic exposure and pharmacokinetics of tramadol and celecoxib in 3 male and 3 female fasted beagle dogs following a single oral dose administration of tablets from examples 2A and 2B were evaluated. The amount of (rac)-tramadol.HCl-celecoxib co-crystal in each formulation was 113.5 mg, corresponding to 50 mg of tramadol.HCl and 63.5 mg of celecoxib. A crossover design was applied with 1 week of washout between administrations. Samples were taken up to 48 hours post-dose.

For tramadol, the overall median value of time at which the maximum plasma concentration occurred ($T_{max}$) was 1.5 hours for tablets example 2A, and 1.0 hour for tablets example 2B, suggesting that the absorption of tramadol was rapid and not affected by the formulation. The rate of exposure as overall mean $C_{max}$ values were 47.2 ng/mL for tablets example 2A and 70.5 ng/mL for tablets example 2B and the extent of exposure as overall mean $AUC_{0-\infty}$ values were 101.2 ng·h/mL for tablets example 2A and 127.8 ng·h/mL in tablets example 2B administration.

For celecoxib the overall median value of time at which the maximum plasma concentration occurred ($T_{max}$) was 2.5 hours for tablets example 2A and 1.5 hours for tablets example 2B, The rate of exposure as overall mean $C_{max}$ values of celecoxib were 1933.3 ng/mL for tablets example 2A and 975.0 ng/mL for tablets example 2B. The extent of exposure as overall mean $AUC_{0-t}$ was 23158.5 ng·h/ml for tablets example 2A and 12828.0 ng·h/ml for tablets 2B.

Example 4b

Study

The aim of this second study was to evaluate and compare the exposure and pharmacokinetics of tramadol and celecoxib in 3 male and 3 female fasted beagle dogs following a single oral dose administration of tablets example 2C versus the concomitant administration of commercial available formulations of tramadol.HCl (Adolonta® IR capsules) and celecoxib (Celebrex® capsules). The amount of (rac)-tramadol.HCl-celecoxib co-crystal (1:1) administered was 2 tablets example 2C of 100 mg corresponding to 88 mg of tramadol.HCl and 112 mg of celecoxib. For the comparators 2 capsules of 50 mg tramadol.HCl (Adolonta® IR) and 1 capsule of 100 mg celecoxib (Celebrex®) were co-administered.

A crossover design was applied with 1 week of washout between administrations. Samples were taken up to 48 hours post-dose.

As in previous study 1, similar overall median $T_{max}$ values were obtained for tramadol, ie 1.3 h for formulation example 2C and 1.0 h for Adolonta® suggesting that the absorption of tramadol was rapid and not affected by the formulation. The exposure rate of tramadol as overall Cmax was 129.3 ng/ml for tablets example 2C and 365.5 ng/ml for Adolonta®. As for tramadol overall exposure extent the $AUC_{0-\infty}$ was 486.5 ng·h/ml for tablets example 2C and 599.7 ng·h/ml in Adolonta® administration.

For celecoxib, overall median time at which the maximum plasma concentration occurred ($T_{max}$) was 2.3 hours for tablets example 2C, and 14.5 hours for Celebrex®. The exposure rate as overall mean $C_{max}$ was 1898.1 ng/ml in example 2C tablets and 1048.5 ng/ml in Celebrex®. As for overall exposure extent the $AUC_{0-\infty}$ was 37780.2 ng·h/ml for tablets example 2C and 22159.8 ng·h/ml in Celebrex® administration.

Example 4c

Summary of Preclinical Pharmacokinetics in Dog

Figure 5:
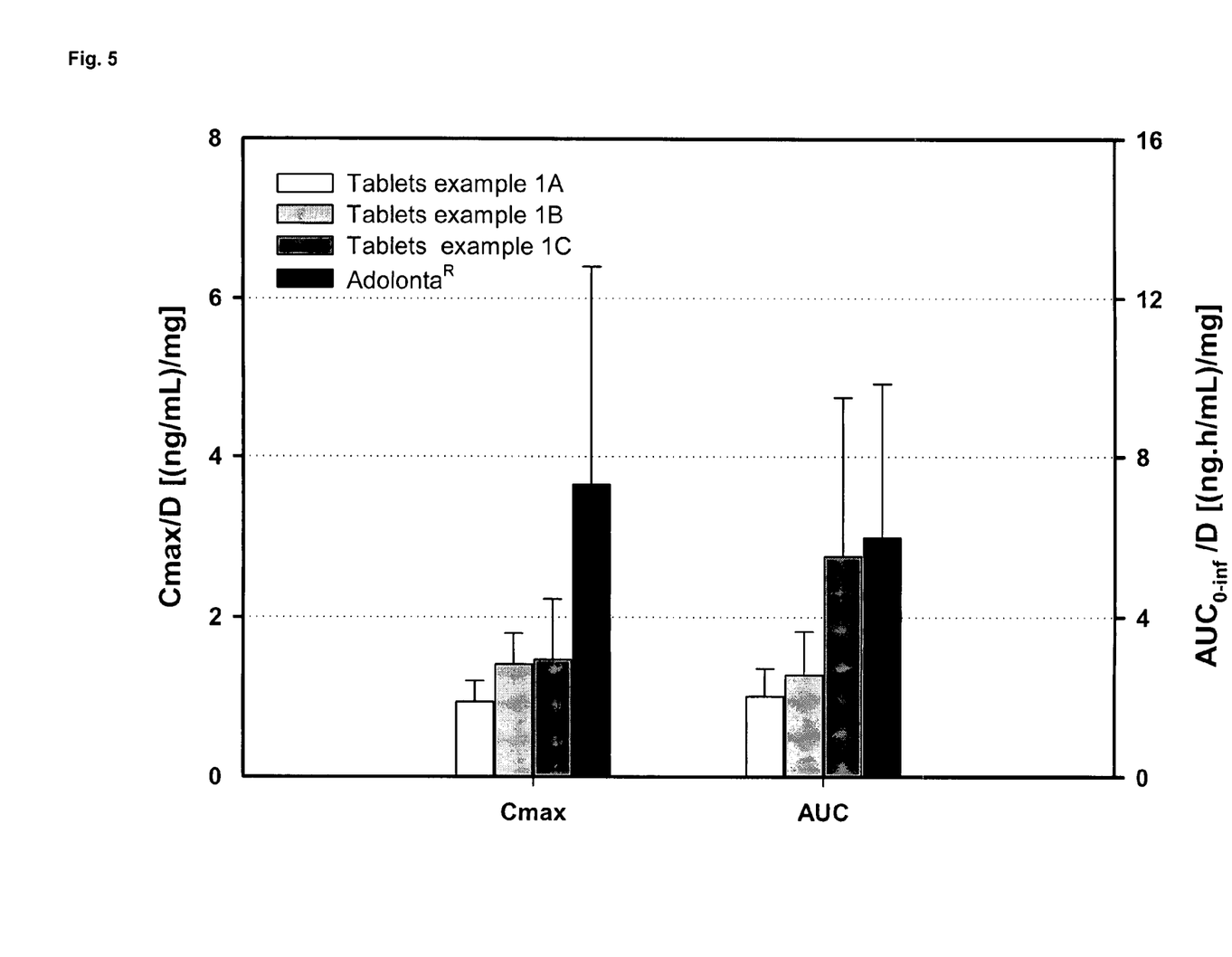
FIG. 5:
Pharmacokinetic parameters of tramadol comparison ($C_{max}$ and AUC) among the three formulations of (rac)-tramadol-celecoxib (1:1) and commercial available formulation.

After comparison of the normalised extent of exposure for tramadol in the three formulations 2A, 2B and 2C of (rac)-tramadol.HCl-celecoxib co-crystal (1:1) when compared with Adolonta® it has been observed a similar behaviour of overall exposure $AUC_{0-\infty}$ for formulation example 2C (0.9-fold). On the other hand, the other two formulations example 2A and example 2B showed lower $AUC_{0-\infty}$ values: 0.3- and 0.4-fold, respectively. In relation to normalised $C_{max}$, all formulations were associated with lower exposure rate (0.3- to 0.4-fold) when compared to Adolonta®. Reduction in peak plasmatic concentrations will ensure better safety for tramadol secondary SNC effects. Similar $T_{max}$ values were observed for the formulations and Adolonta® (see FIG. 5).

| Substance administered | Tramadol·HCl dose (mg) | Mean ± SD | tmax# (h) | Cmax normalized by Dose (ng/ml)/mg | $AUC_{0-\infty}$ normalized by dose (ng·h/ml)/mg |
|---|---|---|---|---|---|
| Tablets of example 2A 113.5 mg × 1 | 50 | Mean | 1.5 | 0.943 | 2.024 |
| | | DE | 1.0-2.5 | 0.264 | 0.693 |
| Tablets of example 2B 113.5 mg × 1 | 50 | Mean | 1.0 | 1.411 | 2.557 |
| | | DE | 1.0-1.5 | 0.387 | 1.088 |
| Tablets of example 2C 100 mg × 2 | 88 | Mean | 1.3 | 1.469 | 5.528 |
| | | DE | 0.5-2.5 | 0.756 | 3.951 |
| Celebrex® 100 mg capsules × 1 | 100 | Mean | 1.0 | 3.655 | 5.997 |
| Adolonta 50 mg capsules × 2 | | DE | 0.5-1.5 | 2.745 | 3.826 |

DE expressed as values range

Figure 6:
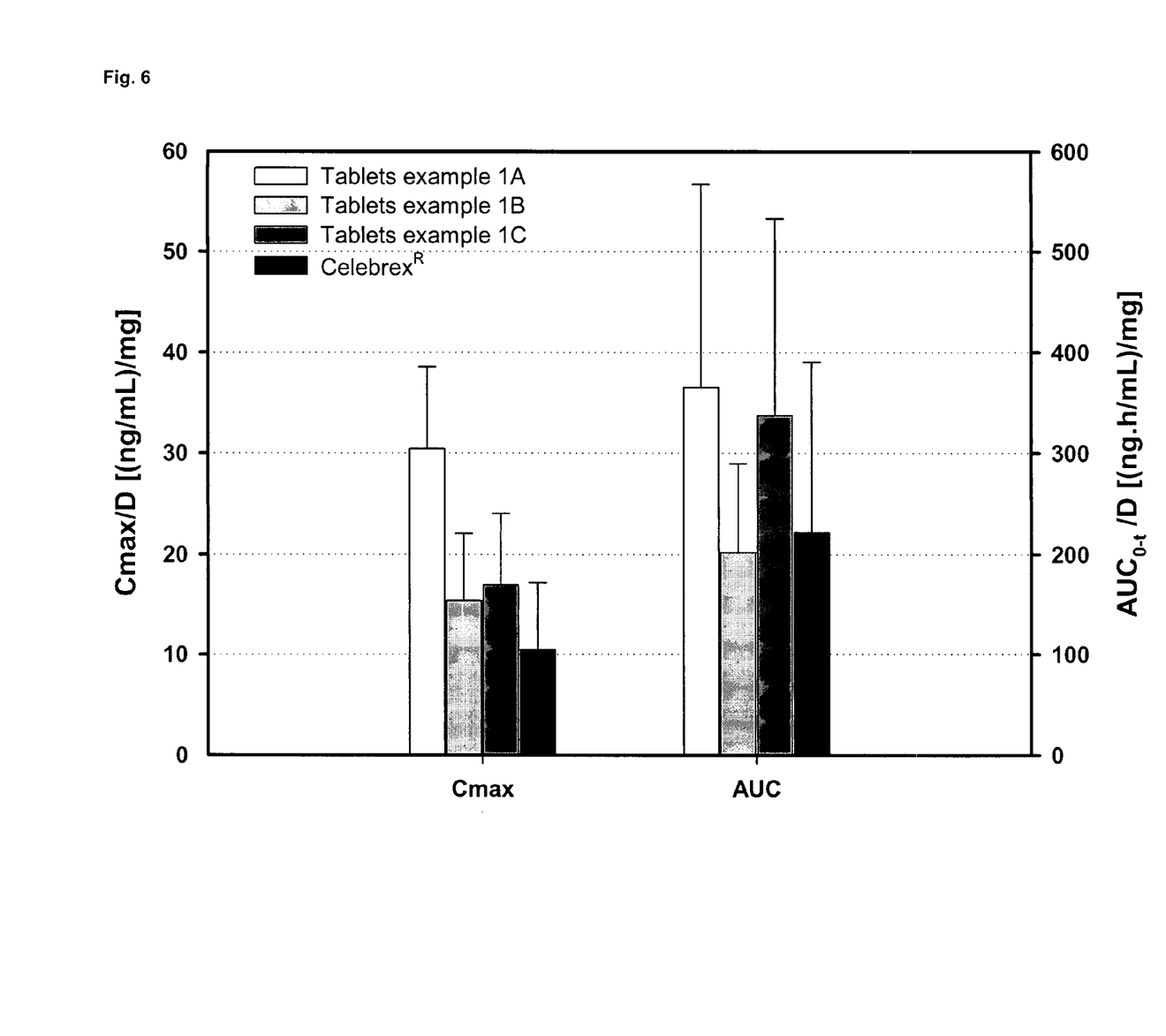
FIG. 6:
Pharmacokinetic parameters of celecoxib comparison ($C_{max}$ and AUC) among the three formulations of (rac)-tramadol-celecoxib (1:1) and commercial available formulation.

For celecoxib, tablet formulation example 2B showed a similar normalised $AUC_{0-t}$ value to that of Celebrex® (0.9-fold), and formulations example 2A and example 2C provided higher values (1.6- and 1.5-fold, respectively). Regarding normalised $C_{max}$, this parameter was 1.5-, 1.6- and 2.9-fold higher than Celebrex® for examples 2B, example 2C and example 2A formulations, respectively (see FIG. 6).

| Substance administered | Celecoxib dose (mg) | Mean ± SD | $t_{max}$# (h) | $C_{max}$ normalized by Dose (ng/ml)/mg | $AUC_{0-\infty}$ normalized by dose (ng·h/ml)/mg |
|---|---|---|---|---|---|
| Tablets of example 2A 113.5 mg × 1 | 63.5 | Mean | 2.5 | 30.446 | 364.700 |
|  |  | DE | 1.5-5.0 | 8.072 | 202.470 |
| Tablets of example 2B 113.5 mg × 1 | 63.5 | Mean | 1.5 | 15.355 | 202.016 |
|  |  | DE | 1.0-4.0 | 6.711 | 87.802 |
| Tablets of example 2C 100 mg × 2 | 112 | Mean | 2.3 | 16.947 | 337.323 |
|  |  | DE | 0.5-24.0 | 7.082 | 195.653 |
| Celebrex ® 100 mg capsules × 1 | 100 | Mean | 14.5 | 10.485 | 221.598 |
| Adolonta 50 mg capsules × 2 |  | DE | 1.0-24.0 | 6.680 | 168.520 |

DE expressed as values range

Summarizing, compared with the individual commercially available products (rac)-tramadol.HCl-celecoxib (1:1) co-crystal tablets from examples 2A, 2B and 2C have not exceeded the exposure for tramadol and showed modulation of peak concentration to lower values respect to Adolonta® IR. This profile ensures efficacy while reduces secondary effects of tramadol resulting in an improvement respect to the commercial form. For celecoxib an increased absorption was obtained both for rate and extent which means a better bioavailability respect to the commercial form.

In conclusion (rac)-tramadol.HCl-celecoxib (1:1) co-crystal tablets examples 2A, 2B, 2C proved to modulate oral absorption of both active principles and showed the capability to obtain a custom-made profile exposure for both tramadol and celecoxib in the (rac)-tramadol.HCl-celecoxib (1:1) co-crystal formulated as tablets.

The invention claimed is:

1. A pharmaceutical composition comprising a co-crystal of (rac)-tramadol.HCl-celecoxib (1:1) and at least a solubility enhancer polymer, wherein the solubility enhancer polymer is selected from polyvinyl caprolactam-polyvinyl acetate-polyethylene glycol graft polymer, copovidone, povidone, polyethylene glycol, and lauroyl macrogel-32 glycerides EP.

2. The pharmaceutical composition according to claim 1 wherein the solubility enhancer polymer is polyvinyl caprolactam-polyvinyl acetate-polyethylene glycol graft copolymer.

3. The pharmaceutical composition according to claim 1 wherein the solubility enhancer polymer is copolymer copovidone.

4. The pharmaceutical composition according to claim 1 wherein the content of solubility enhancer polymer used in the composition lies between 2-50 weight-%.

5. The pharmaceutical composition according to claim 1 being in a form selected from tablet, powder capsules, or formulated by dry granulation, slurries and dry roller compaction.

6. A pharmaceutical composition according to claim 1 in form of a tablet comprising a co-crystal of (rac)-tramadol.HCl-celecoxib (1:1) and at least a solubility enhancer polymer obtainable by a direct compression process.

7. The pharmaceutical composition according to claim 1 further comprising at least a surfactant polymer.

8. The pharmaceutical composition according to claim 7 wherein the surfactant polymer is selected from microencapsulated polisorbate 80, microencapsulated polyoxyl 40-hydrogenated castor oil and sodium lauryl sulphate.

9. The pharmaceutical composition according to claim 1 comprising at least one further pharmaceutically acceptable excipient.

10. The pharmaceutical composition according to claim 9 wherein the pharmaceutically acceptable excipient is a filler selected from a sugar.

11. The pharmaceutical composition according to claim 9 wherein the pharmaceutically acceptable excipient is a lubricant selected from stearyl fumarate, magnesium stearate, talc, and hydrophilic fumed silica, and/or
wherein the pharmaceutically acceptable excipient is a disintegrant selected from crospovidone, croscarmelose sodium, sodium starch glycolate, pregelatinized starch, starch, polacrilin potassium, low-substituted hydroxypropyl cellulose (L-HPC), calcium carboxymethylcellulose, and alginic acid.

12. The pharmaceutical composition according to claim 1, wherein the co-crystal of (rac)-tramadol.HCl and celecoxib (1:1) is characterized in that it shows a Powder X-Ray Diffraction pattern with peaks [2θ] at 7.1, 9.3, 10.2, 10.7, 13.6, 13.9, 14.1, 15.5, 16.1, 16.2, 16.8, 17.5, 18.0, 19.0, 19.5, 19.9, 20.5, 21.2, 21.3, 21.4, 21.8, 22.1, 22.6, 22.7, 23.6, 24.1, 24.4, 25.2, 26.1, 26.6, 26.8, 27.4, 27.9, 28.1, 29.1, 29.9, 30.1, 31.1, 31.3, 31.7, 32.5, 32.8, 34.4, 35.0, 35.8, 36.2 and 37.2[°], with the 2θ values being obtained using copper radiation ($Cu_{K\alpha 1}$ 1.54060 Å); and/or wherein the co-crystal of (rac)-tramadol.HCl and celecoxib (1:1) is characterized in that it shows a Fourier Transform Infra Red pattern with absorption bands at 3481.6 (m), 3133.5 (m), 2923.0 (m), 2667.7 (m), 1596.0 (m), 1472.4 (m), 1458.0 (m), 1335.1 (m), 1288.7 (m), 1271.8 (m), 1168.7 (s), 1237.3 (m), 1168.7 (s), 1122.6 (s), 1100.9 (m), 1042.2 (m), 976.8 (m), 844.6 (m), 820.1 (m), 786.5 (m) 625.9 (m) $cm^{-1}$; and/or
characterized in that the co-crystal of (rac)-tramadol.HCl and celecoxib (1:1) has an orthorhombic unit cell with the following dimensions:
a=11.0323(7) Å
b=18.1095(12) Å
c=17.3206(12) Å; and/or
characterized in that the endothermic sharp peak corresponding to the melting point of the co-crystal of (rac)-tramadol.HCl and celecoxib (1:1) has an onset at 164° C.

13. Process for the production of a pharmaceutical composition according to claim 1 comprising the steps of:
(a) blending the co-crystal of (rac)-tramadol.HCl-celecoxib (1:1) with at least a solubility enhancer polymer according to claim 1 and optionally one or more filler, disintegrant or surfactant polymer or any combination thereof;
(b) optionally adding at least a lubricant;
(c) directly compressing the blend from step (a) or the lubricated blend from step (b) into a tablet;
wherein said pharmaceutical composition is an oral pharmaceutical composition.

14. A pharmaceutical composition according to claim 1 for the treatment of pain.

15. The pharmaceutical composition according to claim 1, wherein the solubility enhancer polymer is selected from copovidone, povidone, polyethylene glycol and lauroyl macrogol-32 glycerides EP.

16. The pharmaceutical composition according to claim 1, wherein the solubility enhancer polymer is selected from copovidone and povidone.

17. The pharmaceutical composition according to claim 4 wherein the content of solubility enhancer polymer used in the composition lies between 8-12 weight-%.

18. The pharmaceutical composition according to claim 4 wherein the content of solubility enhancer polymer used in the composition is approximately 8 weight-%.

19. The pharmaceutical composition according to claim 5, wherein the composition is in the form of a tablet obtainable by a direct compression process.

20. The pharmaceutical composition according to claim 9, wherein the at least one further pharmaceutically acceptable excipient is selected from the group consisting of a filler, a disintegrant and/or a lubricant.

21. The pharmaceutical composition according to claim 9, wherein the pharmaceutically acceptable excipient is an insoluble filler selected from calcium phosphate, calcium carbonate or microcrystalline celluloses like MCC 102 (90 µm) and MCC 200 (200 µm) or wherein the pharmaceutically acceptable excipient is selected from other compounds selected from silicified microcrystalline or compositions containing microcrystalline cellulose, colloidal silicon dioxide, sodium starch glycolate and sodium stearyl fumarate.

22. The pharmaceutical composition according to claim 10, wherein the pharmaceutically acceptable excipient is a filler, wherein the filler is a sugar selected from xylitol, sorbitol, isomalt, erythritol, sucrose, fructose, or dextrose.

23. The pharmaceutical composition according to claim 10, wherein the pharmaceutically acceptable excipient is a filler selected from spray dried mannitol and microcrystalline cellulose.

24. The pharmaceutical composition according to claim 11, wherein the pharmaceutically acceptable excipient is a lubricant selected from stearyl fumarate and talc, and/or wherein the disintegrant is crospovidone.

25. The pharmaceutical composition according to claim 1 for the treatment of pain, wherein the pain is selected from acute pain, chronic pain, neuropathic pain, nociceptive pain, mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica.

* * * * *